United States Patent [19]
Spano et al.

[11] Patent Number: 5,522,863
[45] Date of Patent: Jun. 4, 1996

[54] PULSATING BEHAVIOR MONITORING AND MODIFICATION SYSTEM FOR NEURAL NETWORKS

[75] Inventors: Mark L. Spano, Laurel, Md.; William L. Ditto, Marietta, Ga.; Steven J. Schiff, Rockville, Md.

[73] Assignee: The United States of America as represented by the Secretary of the Navy, Washington, D.C.

[21] Appl. No.: 292,999

[22] Filed: Aug. 19, 1994

Related U.S. Application Data

[63] Continuation-in-part of Ser. No. 930,945, Aug. 19, 1992, Pat. No. 5,342,401.

[51] Int. Cl.⁶ .................................................. A61N 1/18
[52] U.S. Cl. ........................ 607/45; 607/70; 607/72; 607/116; 128/731
[58] Field of Search ..................... 607/43, 45, 46, 607/70, 72, 116, 118; 128/731

[56] References Cited

U.S. PATENT DOCUMENTS

| | | | |
|---|---|---|---|
| 3,850,161 | 11/1974 | Liss | 607/45 |
| 5,025,807 | 6/1991 | Zabara | 607/45 |
| 5,215,086 | 6/1993 | Terry, Jr. et al. | 607/46 |
| 5,299,569 | 4/1994 | Wernicke et al. | 607/45 |

FOREIGN PATENT DOCUMENTS

| | | | |
|---|---|---|---|
| 8501213 | 3/1985 | WIPO | 607/45 |

*Primary Examiner*—William E. Kamm
*Assistant Examiner*—Jeffrey R. Jastrzab
*Attorney, Agent, or Firm*—Jacob Shuster

[57] ABSTRACT

The pulsating behavioral activity of a neural network such as that embodied in a brain tissue slice is monitored by measurement of intervals between spontaneous events to identify the presence of a chaotic regime and determine by real-time calculation a waiting time for electrical pulse intervention pursuant to a behavioral modifying program having a control or anti-control strategy.

14 Claims, 4 Drawing Sheets

PULSATING BEHAVIOR MONITORING AND MODIFICATION SYSTEM FOR NEURAL NETWORKS

The present invention relates in general to monitoring, analyzing and modifying the pulsating behavior of a neural network, and a Continuation-in-Part prior application Ser. No. 07/930,945 filed Aug. 19, 1992 (now U.S. Pat. No. 5,342,401 to Spano et al. issued Aug. 30, 1994), with respect to which this application is a continuation-in-part.

BACKGROUND OF THE INVENTION

Many activities of an apparently random nature have been found to exhibit a deterministic phenomenon known as chaos, including but not limited to irregular pulsating behavior of living animal tissue. Recently, a strategy was developed tending to control a non-linear dynamic system in which a chaotic regime occurs. The critical features of the chaos phenomenon believed to make such control possible are short term predictability and extreme sensitivity of chaotic systems to perturbances of their initial conditions. A key to the control strategy lies in the fact that a chaotic system includes an infinite number of unstable periodic motions and never remains very long in any of such unstable motions, but continually switches from one periodic motion to another to thereby give an appearance of randomness. The chaos control strategy involves measurement of the current system parameter and identification of an unstable fixed point of interest representative of a system state plotted along with its stable and unstable directional manifolds. Such unstable fixed point and its accompanying manifolds shift in response to changes in system-wide parameters so that a feedback providing algorithm was developed for movement of the fixed point and manifolds toward the desired plotted system state point in response to control or modification of a selected system-wide parameter. As an alternative to moving the fixed point in accordance with a system-wide parameter, the system state point itself may be altered and brought closer to the fixed point. The latter strategy was employed to control interbeat intervals of the pulsating activity in living tissue for cardiac arrhythmia stabilization purposes in accordance with real-time calculation with sufficient rapidity to implement corrective control, as disclosed in the aforementioned Spano et al. patent.

A significant characteristic of a neural system associated with brain tissue is the presence of brief aperiodic bursts of focal neuronal activity, referred to as interictal spikes. Such interictal spikes occur between epileptic seizures arising because of nervous system disorders. It is therefore an important object of the present invention to provide a procedure for manipulating chaotic activity, based on the aforementioned study of chaotic regimes, by intervention at irregular times determined from real time calculations involving data obtained by monitoring of brain tissue behavior.

SUMMARY OF THE INVENTION

In accordance with the present invention, a strategy was developed for treatment of epileptic foci in the neuronal network of living brain tissue by monitoring the timing of intervals between system characterizing events such as spontaneous bursts to identify a chaos regime therefrom, involving determination of an unstable fixed point of a system state and accompanying directional manifolds during a learning phase, followed by a chaos control phase during which a waiting time is determined by real-time calculation before delayed intervention is instituted. Such intervention is designed to reliably restore the neural system state to a desired system state represented by an unstable fixed point at the intersection of its stable and unstable directional manifolds plotted as a function of the interval between said monitored burst events. The intervention is delayed by the real-time calculated waiting time, based on switching of the chaotic regime to a periodic pacing condition according to natural system behavior. A minimal time period modifying type of intervention is utilized for reliable shift in system state point.

The aforesaid intervention waiting time is terminated by injection of a stimulus, into the brain tissue to cause corrective movement of the system state toward an unstable fixed point. If the next spontaneous burst corresponds to an interval point close to the unstable fixed point, intervention is suspended until the system state moves away from the unstable fixed point, at which time the behavior modification program is recycled.

In accordance with another embodiment of the invention, a behavior modification program when used to modify pulsating activity of brain tissue by application of stimulus intervention thereto through electrodes, employs an anticontrol chaos strategy based on the recognition that the neural system is characterized by motion of points of spontaneous bursts along a stable manifold path toward the unstable fixed point of the chaotic regime and away from such unstable fixed point along an unstable manifold path by properly delayed stimulus intervention. The stimulus intervention, whether of the anti-control type or of the control strategy type involves injection of either single pulses or trains of pulses of electrical energy of different shapes.

BRIEF DESCRIPTION OF DRAWING FIGURES

A more complete appreciation of the invention and many of its attendant advantages will be readily appreciated as the same becomes better understood by reference to the following detailed description when considered in connection with the accompanying drawings wherein.

DETAILED DESCRIPTION OF PREFERRED EMBODIMENTS

Figure 1:
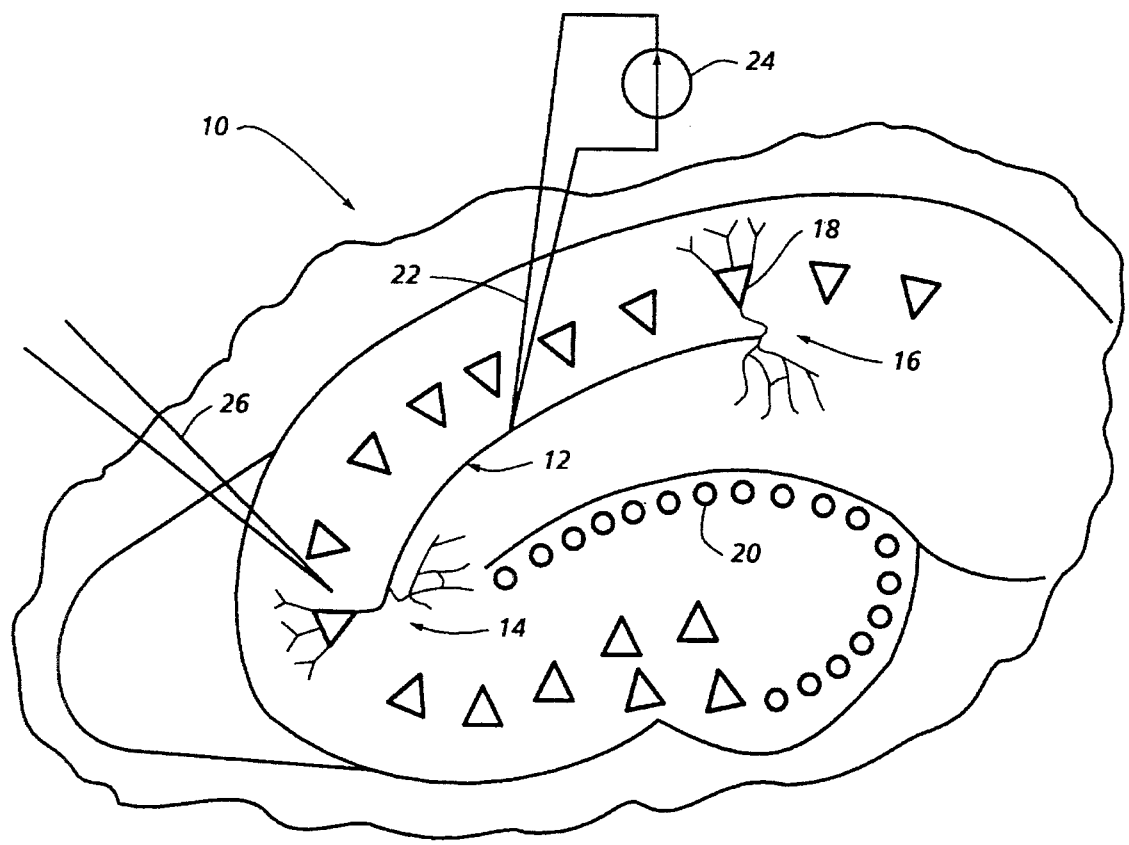
FIG. 1 is an anatomical diagram of a transverse brain tissue slice, with stimulating and recording electrodes attached.

Pursuant to the present invention, a slice 10 of tissue as depicted in FIG. 1 was obtained from the hippocampus of the temporal lobe of a brain decapitated from a female Sprague-Dawley rat weighing between 125 and 150 grams. The brain tissue slice 10, having a thickness of 400 µm, was initiatially perfused by exposure within a perfusion chamber to artificial cerebrospinal fluid containing between 6.5 and 10 mM of potassium (K+) flowing at a rate of 2 ml per minute through the perfusion chamber. The tissue slice 10 during exposure to the fluid was maintained at 32° C. to 35° C. temperature within the perfusion chamber.

As shown in FIG. 1, the anatomy of brain tissue includes a collateral fiber tract 12 (Schaffer collateral fibers) connected to neurons at Cornu Ammonis (CA) regions 14 (CA1) and 16 (CA3). The fiber tract is located between a series of dentate granule cells 20 and a series of pyramidal cells 18 to which the collateral fibers are also connected at the regions 14 (CA1) and 16 (CA3). Tungsten stimulation micro electrodes 22 are attached to the collateral fibers through which electrical pulses are applied from a voltage source 24 as diagrammed in FIG. 1. Also, recording electrodes 26 are embedded in the brain tissue adjacent to region 14. The electrodes 26 utilized were tubular glass needles having a resistance of 2 to 4 M$\Omega$ when filled with 150 mM NaCl.

In accordance with one embodiment of the invention, the perfusate fluid initially utilized was composed of 155 mM $Na^+$, 136 mM $Cl^-$, 3.5 mM $K^+$, 1.2 mM $Ca^{2+}$ and 10 mM dextrose, in order to test the tissue slice 10. Such testing was performed after 90 minutes of tissue incubation in the perfusate fluid by electrical stimulation applied through the electrodes 22. The viability of the neural brain tissue undergoing the foregoing test was confirmed by recording of a unitary population spike in the stratum pyramidable of the brain tissue greater than 2 mV, in response to the delivery of square-wave pulse current stimulation from source 24, having a constant pulse duration of 100 microseconds and a constant magnitude within a range of 50 to 150 microamperes. Upon confirmation of such viability of the brain tissue slice tested, the perfusate fluid was changed to one in which the ionic concentrations of the potassium and chloride components were respectively increased to 8.5 $mM(K^+)$ and 141 $mM(Cl^-)$ in order to induce epileptic activity after exposure of the brain tissue slice to the changed perfusate fluid for 15 to 20 minutes. Such induced epileptic activity was reflected by system characterizing events in the form of spontaneous bursts from regions 14 and 16 as recorded through the electrodes 26.

Figure 2:
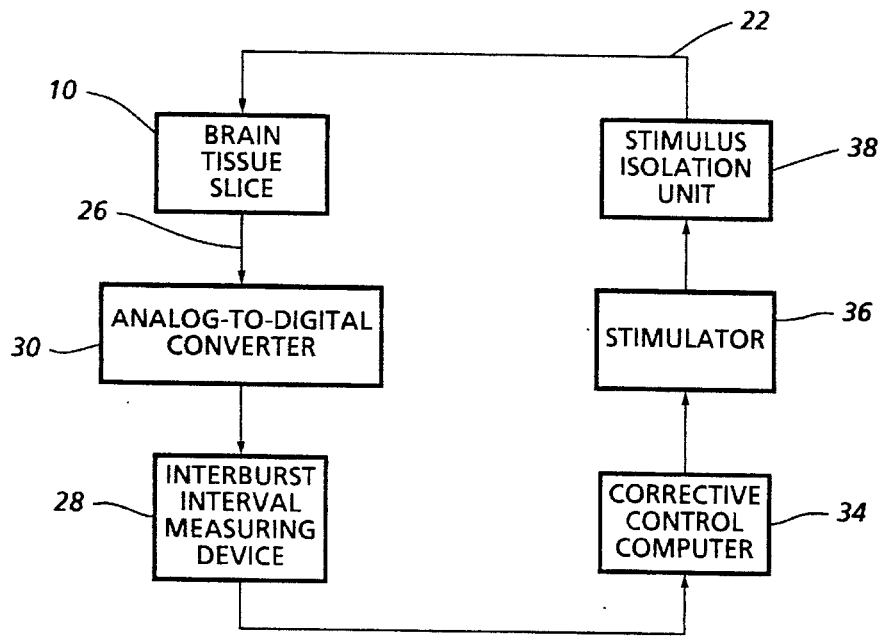
FIG. 2 is a block diagram illustrating a behavioral modifying system in accordance with one embodiment of the invention.

As diagrammed in FIG. 2, the brain tissue of slice 10 when undergoing an epileptic type of activity has its interburst intervals between burst events digitized by a converter 30 through electrodes 26 for measurement by a device 28. The interval data so obtained was generated in accordance with a threshold and peak amplitude detection strategy and was applied to a corrective control computer 34 in order to deliver the aforementioned 100 µsec constant current square-wave pulses to the Schaffer collateral fibers of the tract 12 in the brain tissue by triggering an isolation unit 38 through an associated a stimulator 36. The stimulator 36 and isolation unit 38 utilized are respectively Model Nos. S8800 and S1U7 marketed by Grass Corporation.

Figure 3A:
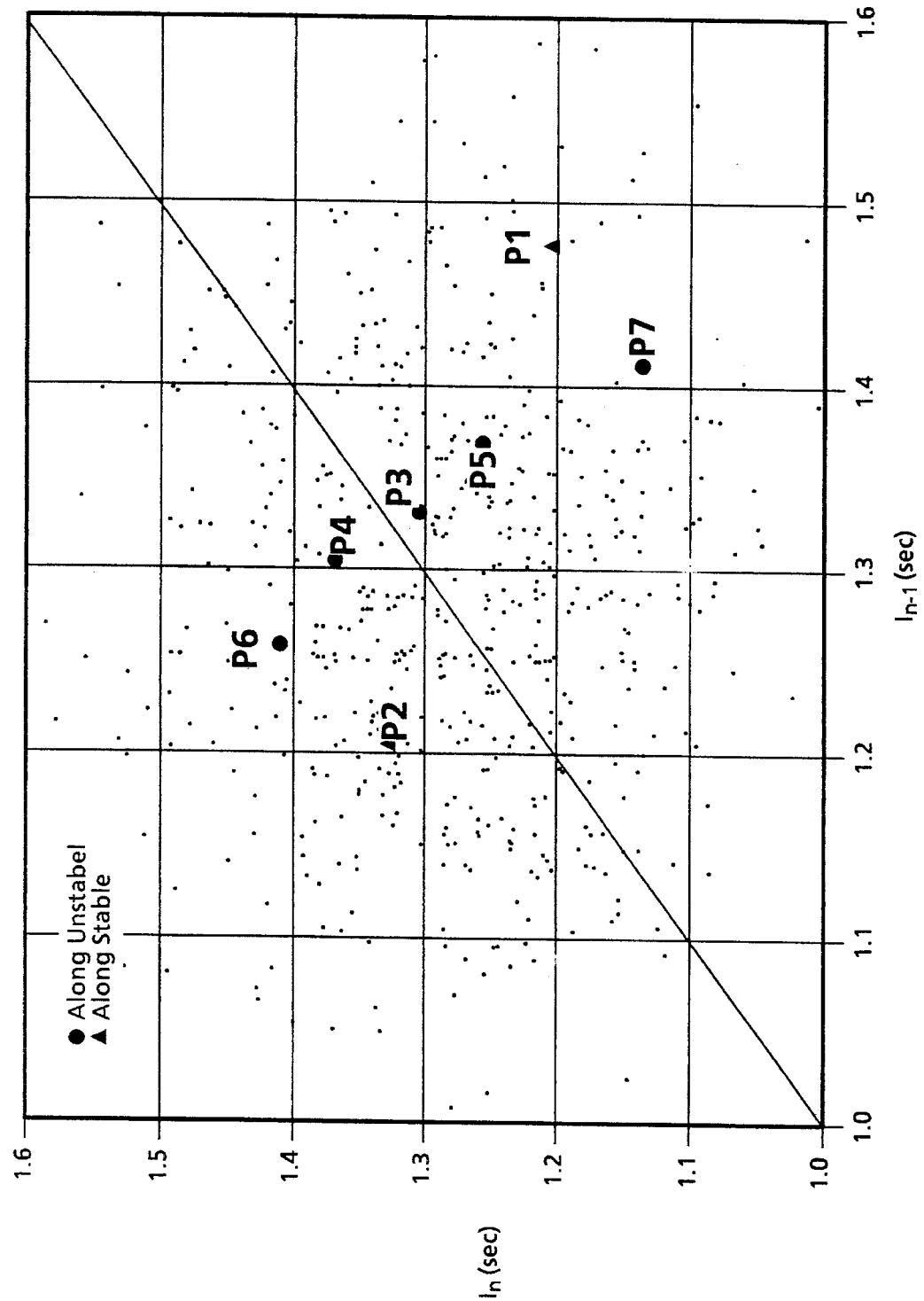
FIGS. 3A and 3B are return maps of interburst interval plots depicting behavioral activity in the neural network of brain tissue such as that diagrammed in FIG. 1.
Figure 3B:
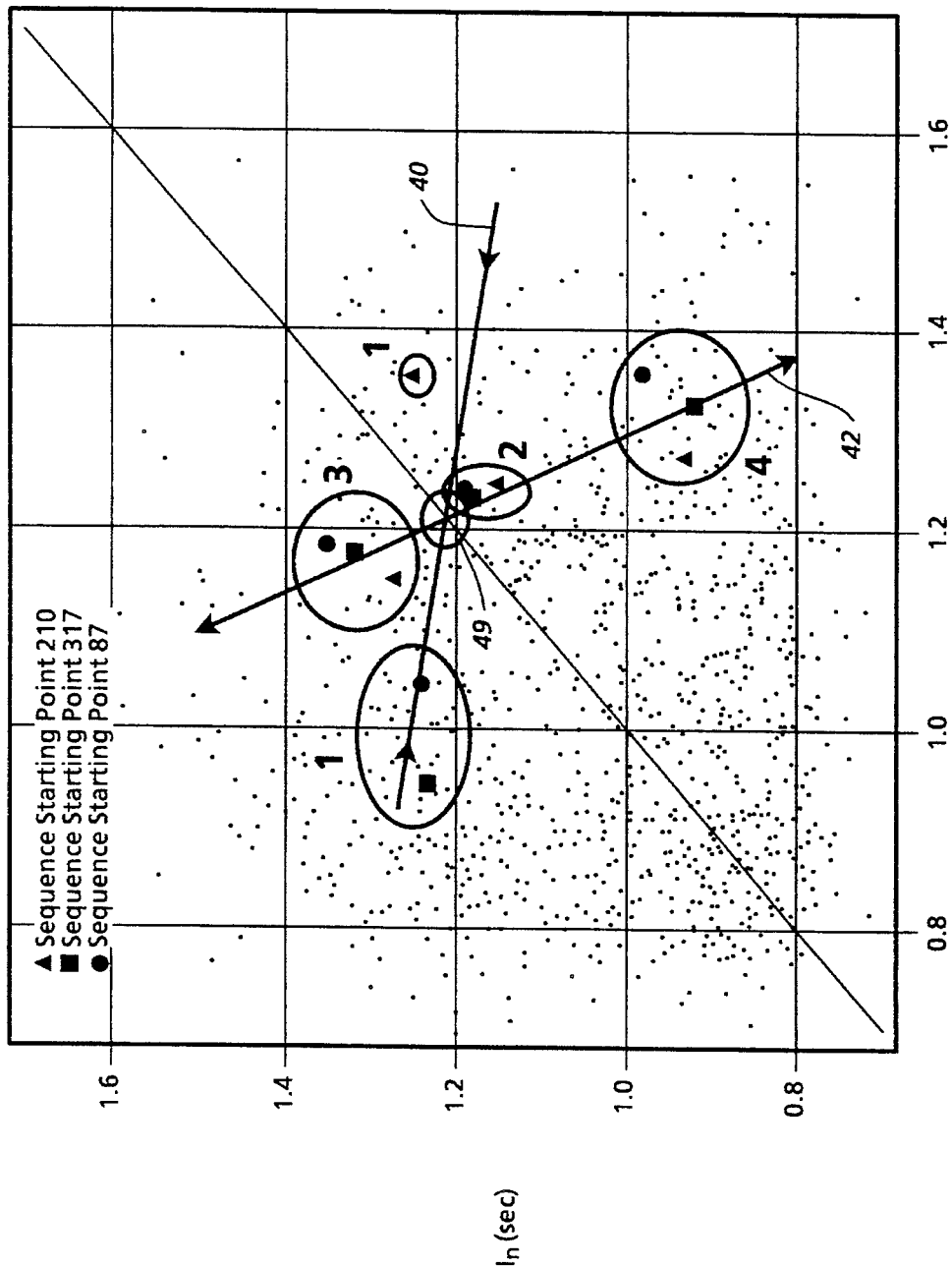

The observed timing of events from a physical chaotic system are aperiodic, such timing evolving transiently from one unstable periodicity to another. The examination of relationships between the timing of such sequential events provides a quantitative understanding of recurring patterns during approach to such unstable periodicities as visualized from a plot which is a type of return map, as shown in FIG. 3A, plotting current interval (In) between events (as monitored by measuring device 28) versus previous interval (In−1). Candidate unstable fixed points, such as point $P_3$ on such a plot are adjacent to a line of identity, where In=In−1. The line of identify is intersected by a stable manifold formed by points $P_1$–$P_3$ and by an unstable manifold formed by points $P_3$–$P_7$. The manifold intersection points in a chaotic system as plotted in FIG. 3B, are known as unstable fixed points which are deterministically approached along the direction of the stable manifold 40, and from which there is exponential divergence along the direction of the unstable manifold 42. Spontaneous activity of the neuronal network of brain tissue is thus evidenced by the tracking of long sequences of plotted data linearly and repeatedly approaching an unstable fixed point along the stable manifold 40 while diverging therefrom along the unstable manifold 42 to demonstrate the exponential departure from the unstable fixed point as expected for chaotic systems. Comparisons of differences between sequences also demonstrates sensitivity to initial conditions characteristic of chaos.

From comparison of many experimental trials on slices of brain tissue from rats, it was found that single pulse stimuli provide chaos control while the use of double pulses as the stimulus intervention, generated at irregular intervals pursuant to a chaos controlling program, could insure higher quality control as compared to single pulse stimulation. Either a single or a double pulsing type of stimulation involving an anti-control strategy type of program was utilized to achieve a reduction in system periodicity, thereby reducing the periodicity of the behavioral activity of the perfused brain tissue.

The activity modifying program utilized in accordance with the present invention by the corrective control computer 34, diagrammed in FIG. 2, is a variation of the chaos controlling algorithm that was successful in treating the ouabain-perfused rabbit heart preparation disclosed in the aforementioned Spano et al. patent. According to the program of the present invention as diagrammed in FIG. 4, data obtained by measurement of intervals between burst events as denoted by block 44, is monitored to identify the unstable fixed points reflecting a chaos regime, as denoted by block 46, during a learning phase 48 of the program. When the intervals between events of the neural network activity being monitored falls within a circle 49 of predetermined radius around an unstable fixed point at the intersection of manifolds 40 and 42 on the return map plot of FIG. 3B, the next interval before pulse stimulation was chosen so as to either place the next system state point on the stable manifold 40 for control purposes, or at a location completely off manifold 40 for anti-control purposes. The pulse stimulation in accordance with the present invention includes, single pulses, double pulses or trains of pulses of different shapes.

With reference once again to FIG. 4, the unstable fixed point is identified to begin determination of stable and unstable directions of approach to and divergence from the identified unstable fixed point and the rates of such approach and divergence as denoted by block 50. Such determination is performed by a local linear least squares fit, excluding data related to higher period behavior in order to conform to a saddle geometry and set criteria for the minimum acceptable linearity of the unstable directional manifold 42. Criteria are also set to limit the rates of approach and divergence along the respective manifolds (eigenvalues). By reason of the properties of a chaotic system reflected on the return map plot of FIG. 3B, the stable manifold 40 has a slope magnitude of less than one (1) while the unstable manifold 42 has a slope of magnitude greater than one (1) to confirm the presence of chaos from the data being monitored.

Figure 4:
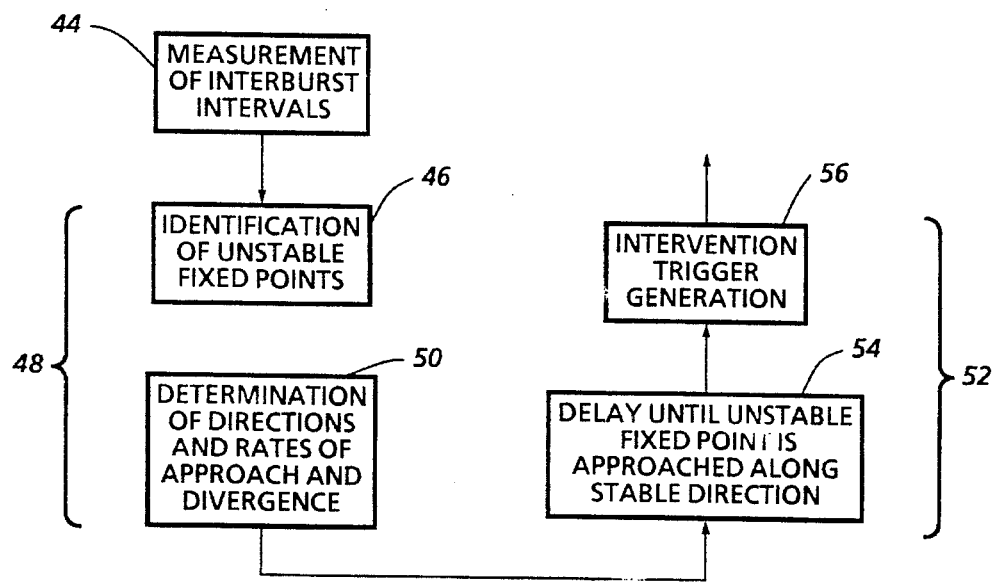
FIG. 4 is a flow chart diagram of the activity modifying program associated with the corrective control computer diagrammed in FIG. 2.

Following the learning phase 48 as above described, a chaos control phase 52 is initiated by waiting until the neural network being monitored executes an approach to the unstable fixed point along the direction of stable manifold 40, as denoted by block 54 in FIG. 4. An intervention triggering signal is then generated pursuant to the strategy hereinbefore described, as denoted by block 56, to modify the timing of the next predicted interburst interval in order to restore the neural system to the stable manifold. The saddle geometry of the data plot as aforementioned, which is inherent in chaotic dynamics, is thereby utilized to restore the neural system to the desired unstable fixed point condition with minimal intervention.

Since the neuronal activity of the brain tissue slice 10 hereinbefore described is known to share similar characteristics with epileptic interictal spike foci, the behavior modifying strategies described may be applicable to the human brain. Furthermore, the effect of breaking up fixed point periodic behavior by the anti-control chaos type of strategy described could provide a different useful stimulus intervention.

Obviously, other modifications and variations of the present invention may be possible in light of the foregoing teachings. It is therefore to be understood that within the scope of the appended claims the invention may be practiced otherwise than as specifically described.

What is claimed is:

1. A method of treating pulsating activity of a neural system having recordable events, including the steps of: measuring intervals between said events; monitoring variation of said measured intervals for identification of an aperiodic chaotic regime; performing a real-time determination of a waiting time following one of said events; and injecting an intervention stimulus into the neural system during the chaotic regime upon completion of the waiting time for behavioral modification of the pulsating activity.

2. The method of claim 1 wherein said intervention stimulus is a single pulse of electrical energy.

3. The method of claim 1 wherein said intervention stimulus is a double pulse of electrical energy.

4. The method of claim 1 wherein said intervention stimulus is a train of pulses of electrical energy of different shapes.

5. A method of treating pulsating activity of a neural system having recordable events, including the steps of: measuring intervals between said events; detecting the measured intervals between the events approaching and diverging from an unstable fixed point along stable and unstable directional manifolds, respectively, having slopes less than and greater than one in magnitude; performing a real-time determination of a waiting time following one of said events; and injecting an intervention stimulus into the neural system during said approaching of the recordable events toward the unstable fixed point along the unstable directional manifold upon completion of the waiting time for behaviorally modifying the pulsating activity.

6. A method of modifying pulsating behavioral activity of a neural system having recordable events, including the steps of: measuring intervals between said events; tracking the measured intervals as points approaching and diverging from an unstable fixed point along stable and unstable directional manifolds, respectively having slopes less than and greater than one, to monitor variation in the measured intervals and identify an aperiodic chaotic regime; performing a real-time determination of a waiting time following one of said events in accordance with a corrective controlling algorithm; and injecting an intervention stimulus into the neural system during the chaotic regime upon completion of the waiting time.

7. A method of modifying pulsating behavioral activity of a neural network having spontaneous events, including the steps of: measuring intervals between said spontaneous events; monitoring variation of said measured intervals for identification of an aperiodic chaotic regime; performing a real-time determination of a waiting time following one of said spontaneous events in accordance with an anti-control chaos algorithm; and injecting an intervention stimulus into the neural network during the identified chaotic regime upon completion of the determined waiting time.

8. Apparatus for treating a neural system undergoing pulsating activity having recordable events, including: means for measuring intervals between said events; means for determination of a pair of directional manifolds along which variation of the measured intervals occurs; means for recognition of a system state, reflected by said measured intervals moving along one of the pair of directional manifolds toward an unstable fixed point thereon intersected by the other of the pair of directional manifolds; performing a real-time determination of a waiting time to divert movement of the system state away from said other of the directional manifolds and means for injecting an intervention stimulus into the neural system upon completion of the waiting time to effect said diverted movement of the system state along said one of the directional manifolds during said displacement thereof from the unstable fixed point.

9. Apparatus for treating a neural system undergoing pulsating activity having recordable events, including: means for measuring intervals between said events; means monitoring variation of the measured intervals for identification of an aperiodic chaotic regime; performing a real-time determination of a waiting time following one of said events; and means injecting an intervention stimulus into the neural system during the chaotic regime upon completion of the waiting time for behavioral modification of the pulsating activity.

10. The apparatus of claim 9 wherein said neural system is embodied in brain tissue having fibers into which the intervention stimulus is injected.

11. The apparatus of claim 9 wherein said recordable events are spontaneous bursts.

12. The apparatus of claim 9 wherein said neural network is embodied in brain tissue having fibers into which electrical pulses are injected as the intervention stimulus.

13. The apparatus of claim 9 wherein said means for identification of the chaotic regime includes: means for determination of a pair of directional manifolds along which said variation of the measured intervals occurs; and means for recognition of a system state, reflected by said measured intervals, moving along one of the directional manifolds toward an unstable fixed point thereon intersected by the other of the pair of directional manifolds along which the system state is displaced from the unstable fixed point.

14. The apparatus of claim 9 wherein said behavioral modifying program is a corrective controlling algorithm.

\* \* \* \* \*